United States Patent
Callu et al.

(10) Patent No.: US 12,421,468 B2
(45) Date of Patent: Sep. 23, 2025

(54) METHOD FOR PURIFYING A FLOW OF NATURAL GAS

(71) Applicant: TOTALENERGIES ONETECH, Courbevoie (FR)

(72) Inventors: Cyrille Callu, Solaize (FR); Loïc Francke, Pau (FR)

(73) Assignee: TOTALENERGIES ONETECH, Courbevoie (FR)

( * ) Notice: Subject to any disclaimer, the term of this patent is extended or adjusted under 35 U.S.C. 154(b) by 86 days.

(21) Appl. No.: 18/275,992

(22) PCT Filed: Nov. 15, 2021

(86) PCT No.: PCT/FR2021/052014
§ 371 (c)(1),
(2) Date: Aug. 4, 2023

(87) PCT Pub. No.: WO2022/167732
PCT Pub. Date: Aug. 11, 2022

(65) Prior Publication Data
US 2024/0101917 A1    Mar. 28, 2024

(30) Foreign Application Priority Data

Feb. 5, 2021    (FR) .................................. FR2101124

(51) Int. Cl.
*C01B 3/24* (2006.01)
*C07C 7/00* (2006.01)
*C10L 3/10* (2006.01)

(52) U.S. Cl.
CPC ....... *C10L 3/101* (2013.01); *C10L 2200/0469* (2013.01); *C10L 2290/02* (2013.01);
(Continued)

(58) Field of Classification Search
CPC ...... C01B 2203/049; C01B 2203/0861; C01B 3/24; C07C 7/00; C07C 7/005;
(Continued)

(56) References Cited

FOREIGN PATENT DOCUMENTS

| EP | 1288182 A1 | 3/2003 | |
|---|---|---|---|
| WO | WO-2018055264 A1 * | 3/2018 | ............. C10L 3/101 |
| WO | WO 2022/167732 A1 | 8/2022 | |

OTHER PUBLICATIONS

WO-2018055264-A1 (Year: 2018).*
International Search Report for PCT/FR2021/052014, dated Feb. 23, 2022, 4 pages.

* cited by examiner

*Primary Examiner* — Ellen M McAvoy
*Assistant Examiner* — Chantel Graham
(74) *Attorney, Agent, or Firm* — Quarles & Brady, LLP

(57) ABSTRACT

Described is a method for purifying a flow of natural gas, comprising the steps: a) processing a portion of the flow by pyrolysis at a temperature in the range from 1000° C. to 2000° C. to decompose the hydrocarbons comprising at least two carbon atoms into elemental carbon and dihydrogen to obtain a processed flow, b) eliminating the elemental carbon present in the processed flow from step a) to obtain a processed flow without elemental carbon; c) when a) and b) have been carried out on a portion of the natural gas flow, mixing the processed flow without any elemental carbon from step b) with the portion of the non-processed flow; d) obtaining a flow of purified natural gas consisting of either the mixture from step c) or the processed flow without any elemental carbon from step b). The invention also relates to preparing fuel from natural gas purified in this manner.

15 Claims, 1 Drawing Sheet

(52) U.S. Cl.
CPC ....... *C10L 2290/24* (2013.01); *C10L 2290/34* (2013.01); *C10L 2290/547* (2013.01)

(58) Field of Classification Search
CPC ... C07C 7/148; C07C 9/04; C10L 2200/0469; C10L 2290/02; C10L 2290/06; C10L 2290/24; C10L 2290/34; C10L 2290/36; C10L 2290/46; C10L 2290/542; C10L 2290/547; C10L 3/101
See application file for complete search history.

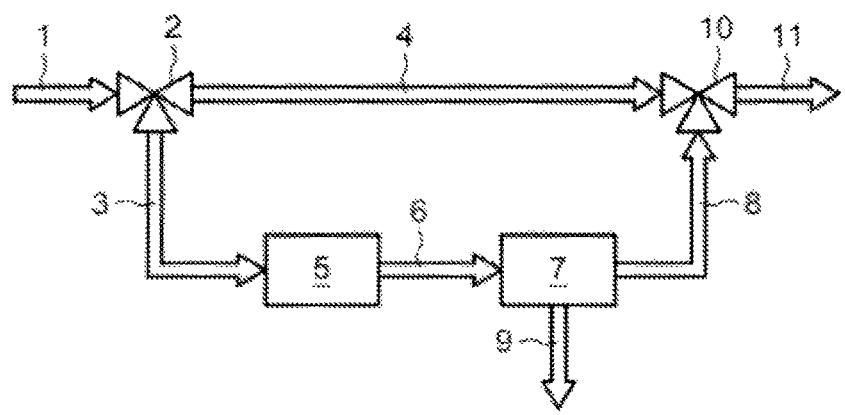

METHOD FOR PURIFYING A FLOW OF NATURAL GAS

CROSS-REFERENCE TO RELATED APPLICATIONS

This application claims priority to and is a 35 U.S.C. § 371 national phase application of PCT/FR2021/052014 (WO2022/167732), filed on Nov. 15, 2021, entitled "Method for Purifying a Flow of Natural Gas", which application claims priority to, and the benefit of, French patent application number FR2101124, filed Feb. 5, 2021, the disclosures of which are incorporated herein by reference in their entirety.

The object of the present invention is a method for purifying a flow of natural gas, in order to reduce its content of undesirable hydrocarbons while increasing its content of methane and dihydrogen.

The method according to the invention is particularly useful for preparing natural gas-based fuels with high energy content and low emission levels.

STATE OF PRIOR ART

Natural gas essentially consists of light $C_1$ to $C_5$ hydrocarbons, including a majority proportion of methane (in particular more than 80 mol %, or even more than 90 mol %), and a minority proportion of higher hydrocarbons such as in particular ethane, propane, butanes and pentanes, the content of which decreases as the number of carbon atoms increases. For example, the ethane content of natural gas may be up to 10 mol %, the propane content up to 1 mol % and the butane content up to 0.3 mol %.

Natural gas may also contain other compounds different from hydrocarbons, in very minor proportions. Depending on where it comes from, natural gas may contain very low levels of nitrogen, carbon dioxide, dihydrogen, hydrogen sulphide, helium and mercaptans.

Natural gas is increasingly used as a fuel to power engines in both private vehicles and special vehicles such as lorries, buses, refuse collection vehicles, etc.

In order to increase energy efficiency of engines running on natural gas on the one hand and to reduce pollutant emissions (especially carbon dioxide) from these engines on the other hand, natural gases used should have the highest possible methane content and the lowest possible content of higher hydrocarbons containing at least two carbon atoms (hereinafter referred to as $C_{2+}$ hydrocarbons).

OBJECT OF THE INVENTION

The purpose of the present invention is to provide an original method for purifying natural gas, which makes it possible to achieve the above objectives of reducing its $C_{2+}$ hydrocarbon content, while at the same time increasing its methane content.

Particularly advantageously, the method also makes it possible to enrich the natural gas with dihydrogen, without generating carbon dioxide.

Thus one object of the present invention is a method for purifying a flow of natural gas, which comprises the following steps:

a) a step of processing at least a portion of said flow by pyrolysis at a temperature in the range of from 1000° C. to 2000° C., so as to decompose hydrocarbons comprising at least two carbon atoms into elemental carbon and dihydrogen $H_2$ and thus obtain a processed flow, then b) a step of eliminating the elemental carbon present in the processed flow from step a) so as to obtain a processed flow free of elemental carbon; then c) when steps a) and b) have been carried out on a portion of the flow of natural gas only, a step of mixing the processed flow free of elemental carbon from step b) with the portion of the non-processed flow; then d) obtaining a flow of purified natural gas consisting either of the mixture from step c) or of the processed flow free of elemental carbon from step b).

The method according to the invention thus consists in subjecting all or part of the flow of natural gas to a process which makes it possible to selectively eliminate $C_{2+}$ hydrocarbons present, such as ethane, propane, butane and pentane, by transforming them by high temperature pyrolysis into elemental carbon and dihydrogen, and then eliminating the elemental carbon resulting from the pyrolysis.

As a result of the elimination of $C_{2+}$ hydrocarbons, the methane content by weight of natural gas increases.

The invention thus makes it possible to increase methane number of the flow of natural gas.

It also makes it possible to control methane number of the natural gas, and to ensure that a processed natural gas is obtained having a constant methane number within a required range, or above a minimum threshold, satisfying a specification for example.

In a manner known per se, the methane number of a fuel gas is a numerical parameter within the range of from 0 to 100, and corresponds to the measurement of the resistance of the gas to knocking by a standardised combustion test in accordance with ISO/TR 22302:2014. Pure methane, used as a reference fuel, has a methane number of 100.

In the case where natural gas is to be used as the basis of an engine fuel, it is essential that it has a constant methane number, in order to guarantee engine performance. For example, specification EN 16732-2 requires a methane number greater than 60, but car manufacturers recommend a methane number greater than 70 (see appendix D of the specification).

Generally speaking, it is sought to obtain a fuel with as high a methane number as possible.

The present invention thus makes it possible, for example, to increase the methane number of the portion of the processed flow from a value below 70 to a value above 80.

In addition, the method according to the invention has the effect of producing dihydrogen ($H_2$) and therefore increasing the $H_2$ content in the flow of natural gas. This dihydrogen, known as "turquoise dihydrogen", is thus produced without carbon dioxide emissions.

When natural gas is to be used as an engine fuel, an increase in its dihydrogen content is beneficial because it reduces carbon dioxide emissions by lowering carbon intensity of the fuel and also by increasing engine efficiency (thus further reducing exhaust $CO_2$ emissions).

By increasing the dihydrogen content of a natural gas-based fuel, a decrease in exhaust particulate emissions, as well as a decrease in emissions of carbon monoxide (CO) and hydrocarbons including methane ($CH_4$) are observed.

The method according to the invention is particularly advantageous in producing natural gas for use as a fuel in an internal combustion engine.

Thus, the present invention also relates to a method for preparing a fuel for an internal combustion engine, comprising:

(i) purifying a flow of natural gas by means of the method according to the invention; and then (ii) conditioning the flow of natural gas resulting from step (i) in the form of compressed natural gas, adsorbed natural gas or liquefied natural gas, preferably in the form of compressed natural gas.

Further objects, characteristics, aspects and advantages of the invention will become even clearer upon reading the following description and examples, and in view of the attached FIG. 1.

FIG. 1 is a schematic representation of the method according to the invention.

In what follows, and unless otherwise indicated, the limits of a range of values are included in this range, especially in the terms "between" and "ranging from . . . to . . . ".

Furthermore, the expressions "at least one" and "at least" used in the present description are respectively equivalent to the expressions "one or more" and "greater than or equal to".

Finally, in a manner known per se, a $C_N$ compound or group is a compound or group containing N carbon atoms in its chemical structure.

DETAILED DESCRIPTION

The method according to the invention is schematically represented in FIG. 1, in which a flow 1 of natural gas is divided into two portions: a first portion 3, conveyed to the unit 5 in which it is processed by pyrolysis, while the other portion 4 of the initial gas flow 1 is not processed. A three-way valve 2 is used to regulate proportion of the flow of natural gas subjected to the process.

Thus, according to a first operating mode, it is possible to close the valve 2, so that the entire flow 1 of natural gas is conveyed to the pyrolysis unit 5 and the non-processed gas flow 4 is zero.

According to a second operating mode, the valve 2 is partially open, so that a portion 3 of the flow 1 of natural gas is conveyed to the pyrolysis step 5.

Preferably, the proportion of the flow 1 of natural gas subjected to steps a) and b) of the method according to the invention (that is the portion 3 of the initial gas flow 1 conveyed to the pyrolysis step 5) accounts for at least 10% by weight of the initial gas flow 1. Preferably, this portion accounts for from 10 to 100% by weight of the initial flow of natural gas, preferably from 20 to 80% by weight.

This proportion can be adjusted as a function of the composition of the initial flow of natural gas (and especially as a function of its $C_{2+}$ hydrocarbon content) and the desired specifications for the purified natural gas, by varying opening of the valve 2.

The portion 3 of the flow of natural gas subjected to steps a) and b) of the method is subjected to a step 5 of pyrolysis 5 at a temperature in the range of from 1000° C. to 2000° C., so as to decompose the $C_{2+}$ hydrocarbons into elemental carbon and dihydrogen ($H_2$).

The processed flow 6 from pyrolysis step 5 undergoes a step 7 in which the elemental carbon generated in step 5 is eliminated and discharged. A flow of elemental carbon 9 is thus recovered and can be reused.

The carbon recovered in this way can be recovered in the form of carbon black (which is a useful raw material especially in inks and tyres), or when the pyrolysis method used leads to specific structural forms of carbon, in the form of graphite, graphene or other forms.

The processed gas flow 8, freed of the elemental carbon from step 7, is finally mixed with the non-processed portion 4 of the flow in the case of the second operating mode described above. A three-way valve 10 makes it possible to regulate proportions of the mixture of the two portions of the flow, namely the processed portion 8 freed of elemental carbon and the non-processed portion 4, especially as a function of their respective compositions and the specifications required for the final flow of purified natural gas 11 resulting from this mixture. Pressure regulators (not represented) can advantageously be positioned upstream of the three-way valve 10 in order to ensure the same pressure for flow 8 and flow 4.

Step a) of Pyrolysis Processing

Step a) of the method according to the invention consists of processing all or part of the flow of natural gas in a pyrolysis unit.

Pyrolysis is a process well known to those skilled in the art, which consists in bringing a product to a very high temperature, so as to cause its thermal decomposition.

In the present invention, it is essential to control the temperature of the pyrolysis step and to maintain it in a range of from 1000° C. to 2000° C. At these temperatures, the hydrocarbons present in the flow of natural gas decompose into elemental carbon C and dihydrogen $H_2$. In this temperature range, the thermal decomposition kinetics of hydrocarbons increase with their number of carbon atoms, which means that the heaviest hydrocarbons (i.e. those with the longest carbon chains) are the first to be decomposed. So, at a given temperature, in view of the decomposition kinetics of the different hydrocarbons present, by controlling the residence time of the gas flow in the pyrolysis unit, it is possible to decompose $C_{2+}$ hydrocarbons without substantially degrading the methane. It is inevitable that a proportion of methane will also be decomposed, but the operating conditions of step a), and especially the pyrolysis temperature and the residence time of the flow in the pyrolysis unit, can be easily adjusted by those skilled in the art so as to maximise decomposition of $C_{2+}$ hydrocarbons and minimise that of methane. Advantageously, the residence time of the flow in the pyrolysis unit is in the range of from 0.01 s to 1 s.

The residence time of the processed gas flow in the pyrolysis unit can be controlled by adjusting its flow rate.

Preferably, the pyrolysis temperature in step a) is in the range of from 1100 to 1600° C., preferably from 1200 to 1500° C.

Performing step a) is not limited to a specific pyrolysis technique, and all known pyrolysis techniques can be used as long as they enable the required temperatures to be reached and the residence time of the flow or portion of the flow of natural gas processed in step a) to be precisely controlled, so as to maximise the selective decomposition of $C_{2+}$ hydrocarbons.

According to a first embodiment, the pyrolysis step is carried out by heating the flow or the portion of the flow of natural gas by means of a hot plasma.

Hot plasma can be generated using different technologies known to those skilled in the art, such as especially microwaves, plasma torches or alternating current.

Microwave technology consists in using one or more standard (athermal) microwave generation modules with a microwave/gas coupling in a reactor, so as to produce hot plasma from the natural gas. This plasma is initiated and maintained by the electron transfer due to microwaves. It is possible to use several modules in series, depending on the conversion rate wanted.

Plasma torch technology is used to introduce plasma jets into the chamber through which the flow of natural gas passes. The temperature of the torch (generally greater than or equal to 6000° C.) enables the chamber to be brought to the temperature required for selective pyrolysis of natural gas.

Alternating current technology consists in generating heat by passing an alternating current through the reactor in which the processed flow of natural gas circulates. The alternating current creates electric arcs in the reactor. It is the energy from these arcs that heats natural gas, transforms it into a plasma and enables it to decompose.

According to a second embodiment, the pyrolysis step is carried out by circulating the flow or portion of the flow of natural gas in a column filled with molten metal. Any suitable metal with a melting point in the required temperature range can be used for this purpose, such as, for example, indium (In), gallium (Ga), bismuth (Bi), tin (Sn), lead (Pb) and nickel (Ni).

According to a third embodiment, the pyrolysis step is carried out by heating the flow or portion of the flow of natural gas using shock waves.

This technology consists in using the kinetic energy of a wave train, created either by pressure differences or by a high-pressure electromagnetic valve, in a shock tube to heat the natural gas to the required temperature. The system can be optimised by using a rotor to improve conversion efficiencies.

Within the scope of a so-called open loop configuration method, the natural gas arrives under pressure (70 bar) and the outflow is around 30 bar. To improve the conversion rate, it is possible to use a so-called closed loop configuration method, which allows a portion of the processed flow of natural gas to be recirculated to increase conversion rates of the gas to be processed.

According to a fourth embodiment, the pyrolysis step is carried out by heating the flow or portion of the flow of natural gas by induction, either directly or indirectly, for example via a metal or carbon catalyst.

Regardless of the pyrolysis technology implemented, it is possible to implement several process units (or reactors) in series, and/or to recycle a portion of the processed gas flow to the pyrolysis unit or reactor, in order to achieve the desired rate of decomposition of $C_{21}$ hydrocarbons.

At the end of step a), a processed flow containing a significant proportion of methane, elemental carbon generally in the solid state, and dihydrogen is obtained.

The content of $C_{2+}$ hydrocarbons in the processed flow is generally less than 0.5 mol %, preferably less than 0.1% and better still equal to 0 mol %.

Step b) of Carbon Elimination

Step b) of the method according to the invention consists in eliminating elemental carbon from the processed flow of natural gas resulting from step a).

Different technologies can be used for this purpose, and the invention is not limited to the use of any particular technology.

According to a first embodiment, step b) is carried out by circulating the processed flow of natural gas from step a) in a molten salt bath.

This molten salt bath traps the carbon that solidifies in the bath, thereby recovering a gas flow freed of elemental carbon. The solid carbon rises to the surface of the molten salt bath, from which it is then regularly eliminated mechanically.

According to a second embodiment, step b) is carried out by cooling the processed flow of natural gas from step a) (for example by means of a heat exchanger, for example supplied with cold water) and then circulating it in one or more mechanical separation devices such as especially one or more cyclones, one or more filters.

These types of devices, known per se, enable the carbon to be recovered in the form of solid particles. It may be advantageous to implement several cyclones and/or several filters arranged in series.

A particularly preferred alternative to this method consists in circulating said flow of processed natural gas in mechanical separation devices comprising one or more cyclones, followed by one or more filters. The cyclone enables the particles to coalesce in order to improve filtration efficiency.

At the end of step b), a flow is obtained which is free of elemental carbon and enriched with dihydrogen, while containing a significant proportion of methane. This flow from step b) is also free of $C_{2+}$ hydrocarbons. It typically contains an amount of dihydrogen ranging from 10 to 30 mol %, preferably from 10 to 20 mol %.

By "free of elemental carbon", it is meant a flow with an elemental carbon content of less than 0.1 mol %.

By "free of $C_{2+}$ hydrocarbon", it is meant a flow with a $C_{2+}$ hydrocarbon content of less than 0.5 mol %.

The fuel preparation method According to an advantageous embodiment of the invention, the flow of natural gas purified by means of the method described above is then used to prepare a fuel for an internal combustion engine.

The fuel thus obtained may be in the form of compressed natural gas (CNG, at a pressure of approximately 200 bar), adsorbed natural gas (ANG) or liquefied natural gas (LNG, at a temperature of approximately −160° C.). Preferably, it is in the form of compressed natural gas, that is maintained at a high pressure, typically 200 bar (2.107 Pa).

The fuel may also comprise one or more additives, which may be chosen from all the additives usually used in the formulation of natural gas-based fuels.

Reodorant additives may be mentioned, which especially include sulphur compounds (tetrahydrothiophene (THT) or methylmercaptan (or methanethiol)), and may be present in contents ranging in particular from 15 to 40 mg/m$^3$.

The following example is simply intended to illustrate the invention without limiting the scope thereof.

Example

The flow of natural gas used in this example has the composition detailed in Table 1 below.

TABLE 1

| Compound | Content (in mole %) |
| --- | --- |
| Nitrogen $N_2$ | 0.423 |
| Methane $CH_4$ | 90.678 |
| Ethane $C_2H_6$ | 7.949 |
| Propane $C_3H_8$ | 0.743 |
| Iso-butane $iC_4H_{10}$ | 0.074 |
| Normal-butane $nC_4H_{10}$ | 0.112 |
| Iso-pentane $iC_5H_{12}$ | 0.016 |
| Normal-pentane $nC_5H_{12}$ | 0.006 |

This flow of natural gas having a rate of 220 tonnes/day is processed in accordance with the method of the invention, as follows:
 a) all or part of the gas flow is processed by pyrolysis, in a microwave plasma reactor, consisting of an injection tube around which a waveguide supplies microwaves which create a plasma within the injection tube, thus enabling pyrolysis. The microwaves are created by a magnetron, but a semiconductor microwave generator can also be employed. The temperature within the injection tube is maintained in the range of from 1200 to 1500° C.

In this reactor, all the $C_2$ to $C_5$ hydrocarbons and approximately 5% of the methane are decomposed into elemental carbon C and dihydrogen $H_2$. The operating conditions chosen thus lead to high selectivity in favour of the conversion of $C_{2+}$ hydrocarbons;

b) the processed flow leaving the plasma reactor then circulates in a separation unit containing a cyclone followed by a filter so as to separate carbon in the form of solid particles and thus recover a flow without any elemental carbon and $C_{2+}$ hydrocarbons, and enriched with dihydrogen. The processed flow enters the cyclone at a temperature of around 250° C. and exits at a temperature of 50° C.

The proportion by weight of the gas flow subjected to steps a) and b) below is varied.

In the first test, the entire gas flow is processed (100% proportion).

In subsequent tests, only a portion of the gas flow is processed, by varying the proportion of the processed gas flow from 20 to 80% by weight, and this processed portion of the flow, freed of elemental carbon from steps a) and b), is then mixed with the non-processed portion of the initial flow.

The amounts of the different compounds present in the final flow of purified natural gas and the amount of elemental carbon C recovered are detailed in Table 2 below, for each of the tests.

TABLE 2

| Proportion of the processed gas flow | $H_2$ flow rate (tonnes/day) | C flow rate (tonnes/day) | $CH_4$ flow rate (tonnes/day) |
|---|---|---|---|
| 100% | 5.8 | 21.1 | 192.2 |
| 80% | 4.6 | 16.9 | 193.8 |
| 60% | 3.5 | 12.6 | 195.3 |
| 40% | 2.3 | 8.4 | 196.9 |
| 20% | 1.2 | 4.2 | 198.4 |

Table 3 below shows the molar content of dihydrogen $H_2$ in the final flow of purified natural gas.

TABLE 3

| Proportion of processed gas flow | $H_2$ content of the flow of purified natural gas (mole %) |
|---|---|
| 100% | 24.1% |
| 80% | 19.1% |
| 60% | 14.2% |
| 40% | 9.4% |
| 20% | 4.7% |

The invention claimed is:

1. A method for purifying a flow (1) of natural gas, comprising the following steps:
    a) a step (5) of processing at least a portion (3) of said flow (1) by pyrolysis at a temperature in the range of from 1000° C. to 2000° C., so as to decompose hydrocarbons comprising at least two carbon atoms into elemental carbon and dihydrogen $H_2$ and thus obtain a processed flow (6), then
    b) a step (7) of eliminating the elemental carbon present in the processed flow (6) from step a) so as to obtain a processed flow (8) free of elemental carbon; then
    c) when steps a) and b) have been carried out on a portion of the flow (1) of natural gas only, a step (10) of mixing the processed flow (8) free of elemental carbon from step b) with the portion (4) of the non-processed flow; then
    d) obtaining a flow of purified natural gas (11) consisting either of the mixture (10) from step c) or of the processed flow (8) free of elemental carbon from step b).

2. The method according to claim 1, wherein the pyrolysis temperature in step a) is in the range of from 1100 to 1600° C.

3. The method according to claim 1, wherein the pyrolysis step is carried out by heating the flow or the portion of the flow of natural gas by means of a hot plasma.

4. The method according to claim 1, wherein the hot plasma is generated by microwaves, plasma torch or alternating current.

5. The method according to claim 1, wherein the pyrolysis step is carried out by circulating the flow or portion of the flow of natural gas in a column filled with molten metal.

6. The method according to claim 1, wherein the pyrolysis step is carried out by heating the flow or the portion of the flow of natural gas by shock waves.

7. The method according to claim 1, wherein the pyrolysis step is carried out by heating the flow or the portion of the flow of natural gas by induction, either directly or indirectly, for example via a catalyst.

8. The method according to claim 1, wherein the proportion of the flow of natural gas (1) subjected to steps a) and b) accounts for at least 10% by weight of the gas flow (1).

9. The method according to claim 1, wherein step b) is carried out by circulating the processed flow of natural gas from step a) in a molten salt bath.

10. The method according to claim 1, wherein step b) is carried out by cooling the processed flow of natural gas from step a) and then circulating it in one or more mechanical separation devices.

11. The method according to claim 10, wherein the mechanical separation devices comprise one or more cyclones, followed by one or more filters.

12. A method for preparing a fuel for an internal combustion engine, comprising:
    (i) purifying a flow of natural gas using the method as defined in claim 1; and then
    (ii) conditioning the flow of natural gas from step (i) as compressed natural gas, adsorbed natural gas or liquefied natural gas, preferably as compressed natural gas.

13. The method according to claim 1, wherein the pyrolysis temperature in step a) is in the range of from 1200 to 1500° C.

14. The method according to claim 1, wherein the proportion of the flow of natural gas (1) subjected to steps a) and b) accounts for from 10 to 100% by weight of said flow.

15. The method according to claim 1, wherein the proportion of the flow of natural gas (1) subjected to steps a) and b) accounts for from 20 to 80% by weight of said flow.

* * * * *